United States Patent [19]
Sorge et al.

[11] Patent Number: 5,354,656
[45] Date of Patent: Oct. 11, 1994

[54] METHOD OF DNA SEQUENCING

[75] Inventors: Joseph A. Sorge, Rancho Santa Fe; William D. Huse, Del Mar, both of Calif.

[73] Assignee: Stratagene, La Jolla, Calif.

[21] Appl. No.: 416,021

[22] Filed: Oct. 2, 1989

[51] Int. Cl.$^5$ .............. C12Q 1/68; C07H 21/04; C12N 15/00
[52] U.S. Cl. .............. 435/6; 536/24.3; 536/24.33; 935/77; 935/78
[58] Field of Search .............. 435/6; 536/27, 24.3, 536/24.33; 935/77, 78

[56] References Cited

U.S. PATENT DOCUMENTS 4,683,195  7/1987  Mullis et al. ..................... 435/6

FOREIGN PATENT DOCUMENTS 0297397  1/1989  European Pat. Off. .

OTHER PUBLICATIONS

Maniatis et al, Molecular Cloning: A Laboratory Manual, 1982, Cold Spring Harbor Laboratory, p. 102.
Sanger et al, Proc. Natl. Acad. Sci. USA, Dec. 1977, vo. 74, No. 12, pp. 5463–5467.
Leader et al., *DNA*, 5:235–238 (1986).
Church et al., *Proc. Natl. Acad. Sci.*, 81:1991–1995 (1984).
Guo et al., *Nucleic Acids Res.*, 10:2065–2085 (1982).
Guo et al., *Meth. Enz.*, 100:60–97.
Maxam and Gilbert, *Meth. Enzymol.*, 65:499–561 (1977).

*Primary Examiner*—Mindy B. Fleisher
*Attorney, Agent, or Firm*—Ronni L. Sherman

[57] ABSTRACT

An improved method of determining the nucleotide base sequence of DNA is disclosed. The method comprises preparing a DNA substrate comprising a set of molecules, each having a template strand and a primer strand, wherein the 3' ends of the primer strands terminate at about the same nucleotide position on the template strands of the molecules within each set. DNA synthesis is induced to obtain labeled reaction products comprising newly synthesized DNA complementary to the template strands using the 3' ends of the primer strands to prime DNA synthesis, labeled nucleoside triphosphates, and at least one modified nucleoside triphosphate, wherein the modified nucleoside triphosphate is selected to substantially protect newly synthesized DNA from cleavage. The labeled reaction products are cleaved at one or more sites to obtain labeled DNA fragments wherein the newly synthesized DNA is substantially protected from cleavage at the selected site or sites. The labeled DNA fragments are separated and their nucleotide base sequence is identified by suitable means.

36 Claims, 5 Drawing Sheets

TIMEPOINT

0 MIN

```
                              TEMPLATE
5'                                                                              3'
TAGCACTATTACCGGGATACGTACTACAGTTACGTACAGTCAACCGGGTATTACAGTACACCGGGATATCT
                                                                         PRIMER
    3' TGATAATGGCCCTATGCATGATGTCAATGCATGTCAGTTGGCCCATAATGTCATGTGGCCCTA 5'
```

10 MIN

```
                              TEMPLATE
5'                                                                              3'
TAGCACTATTACCGGGATACGTACTACAGTTACGTACAGTCAACCGGGTATTACAGTACACCGGGATATCT
      ***        *
     3' ddATGGCCCTATGCATGATGTCAATGCATGTCAGTTGGCCCATAATGTCATGTGGCCCTA 5'      ↑
        ***        *
      3' ddTGGCCCTATGCATGATGTCAATGCATGTCAGTTGGCCCATAATGTCATGTGGCCCTA 5'      |
         ***        *
       3' ddGGCCCTATGCATGATGTCAATGCATGTCAGTTGGCCCATAATGTCATGTGGCCCTA 5'
          ***        *
        3' ddGCCCTATGCATGATGTCAATGCATGTCAGTTGGCCCATAATGTCATGTGGCCCTA 5' PRIMER
           ***        *
         3' ddCCCTATGCATGATGTCAATGCATGTCAGTTGGCCCATAATGTCATGTGGCCCTA 5'      |
            **         *
          3' ddCCTATGCATGATGTCAATGCATGTCAGTTGGCCCATAATGTCATGTGGCCCTA 5'      ↓
             *         *
           3' ddCTATGCATGATGTCAATGCATGTCAGTTGGCCCATAATGTCATGTGGCCCTA 5'
                  ←
                POLYMERASE
```

20 MIN

```
                              TEMPLATE
5'
TAGCACTATTACCGGGATACGTACTACAGTTACGTACAGTCAACCGGGTATTACAGTACACCGGGATATCT
                                                 ***
                                    3' ddAGTTGGCCCATAATGTCATGTGGCCCTA 5'    ↑
                                          ***
                                      3' ddGTTGGCCCATAATGTCATGTGGCCCTA 5'   |
                                           ***
                                       3' ddTTGGCCCATAATGTCATGTGGCCCTA 5'
                                            ***
                                        3' ddTGGCCCATAATGTCATGTGGCCCTA 5' PRIMER
                                             ***
                                         3' ddGGCCCATAATGTCATGTGGCCCTA 5'   |
                                              ***
                                          3' ddGCCCATAATGTCATGTGGCCCTA 5'   ↓
                                               ***
        * = METHYL                         3' ddCCCATAATGTCATGTGGCCCTA 5'
                                                    ←
                                                  POLYMERASE
```

FIG. 3

TIMEPOINT
0 MIN

```
5'                                                   TEMPLATE              3'
TAGCACTATTACCGGGATACGTACTACAGTTACGTACAGTCAACCGGGTATTACAGTACACCGGGATATCT

3' TGATAATGGCCCTATGCATGATGTCAATGCATGTCAGTTGGCCCATAATGTCATGTGGCCCTA 5'
                    ↑                          ↑    PRIMER    ↑
                  Nci I                      Nci I          Nci I
                  SITE                       SITE           SITE
```

SEQUENCE
PROTECTED
↓

10 MIN            ENZYME          ENZYME
                  CUTS            CUTS

```
         ***    *
3' ddATGGCCCTATGCAT  GATGTCAATGCATGTCAGTTGGC   CCATAATGTCATGTGGC   CCTA 5'
       ***    *
3' ddTGGCCCTATGCAT   GATGTCAATGCATGTCAGTTGGC   CCATAATGTCATGTGGC   CCTA 5'
      ***    *
3' ddGGCCCTATGCAT    GATGTCAATGCATGTCAGTTGGC   CCATAATGTCATGTGGC   CCTA 5'
     ***    *
3' ddGCCCTATGCAT     GATGTCAATGCATGTCAGTTGGC   CCATAATGTCATGTGGC   CCTA 5'
    ***    *
3' ddCCCTATGCAT      GATGTCAATGCATGTCAGTTGGC   CCATAATGTCATGTGGC   CCTA 5'
    **    *
3' ddCCTATGCAT       GATGTCAATGCATGTCAGTTGGC   CCATAATGTCATGTGGC   CCTA 5'
     *    *
3' ddCTATGCAT        GATGTCAATGCATGTCAGTTGGC   CCATAATGTCATGTGGC   CCTA 5'
                                            ↓                   ↓
```

SEQUENCE
PROTECTED
↓                 ENZYME
                  CUTS
20 MIN

```
                        ***
          * = METHYL
                   3' ddAGTTGGCCCATAATGTCATGTGGC  CCTA 5'
                          ***
                    3' ddGTTGGCCCATAATGTCATGTGGC CCTA 5'
                          ***
                     3' ddTTGGCCCATAATGTCATGTGGC CCTA 5'
                          ***
                      3' ddTGGCCCATAATGTCATGTGGC CCTA 5'
                          ***
                       3' ddGGCCCATAATGTCATGTGGC CCTA 5'
                          ***
                        3' ddGCCCATAATGTCATGTGGC CCTA 5'
                          ***
                         3' ddCCCATAATGTCATGTGGC CCTA 5'
                                               ↓
```

FIG. 4

METHOD OF DNA SEQUENCING

FIELD OF THE INVENTION

The present invention relates to methods for determination of the nucleotide base sequence of nucleic acids, particularly DNA.

BACKGROUND OF THE INVENTION

DNA sequence information represents the information required for gene organization and regulation of most life forms. Accordingly, the development of reliable methodology for sequencing DNA has contributed significantly to an understanding of gene structure and function.

Generally, strategies for determining the nucleotide sequence of DNA involve the generation of a DNA substrate i.e., DNA fragments suitable for sequencing a region of the DNA, enzymatic or chemical reactions, and analysis of DNA fragments that have been separated according to their lengths to yield sequence information. More specifically, to sequence a given region of DNA, labeled DNA fragments are typically generated in four separate reactions. In each of the four reactions, the DNA fragments typically have one fixed end and one end that terminates sequentially at each of the four nucleotide bases, respectively. The products of each reaction are fractionated by gel electropheresis on adjacent lanes of a polyacrylamide gel. As all of the nucleotides are represented among the four lanes, the sequence of a given region of DNA can be determined from the four "ladders" of DNA fragments. Presently, there are two general approaches available to generate ladders of DNA fragments for determination of the nucleotide base sequence of DNA of interest. One approach involves nucleotide specific chemical modification and cleavage reactions as described by Maxam and Gilbert, *Meth. Enz.*, 65:499 (1980). A second approach, which involves primer extension reactions in the presence of nucleotide specific chain terminators as described by Sanger et al., *Proc. Natl. Acad. Sci.*, 74:5463 (1977), is most commonly used for sequence determination.

The Maxam-Gilbert technique, supra, relies upon the base-specific chemical cleavage of the DNA to be sequenced. After the DNA substrate is end labeled, it is subjected to chemical reactions designed to cleave the DNA at positions adjacent to a given base or bases. The labeled DNA fragments will, therefore, have a common labeled terminus while the unlabeled termini will be defined by the positions of chemical cleavage. This results in the generation of DNA fragments which can be separated by gel electrophoresis and identified. Alternatively, unlabeled DNA fragments can be separated after complete restriction digestion and partial chemical cleavage of the DNA, and hybridized with probes homologous to a region near the region of the DNA to be sequenced. See, Church et al., *Proc. Natl. Acad. Sci.*, 81:1991 (1984).

The Sanger method, supra, involves the enzymatic synthesis of a strand complementary to the DNA to be sequenced. Essentially, a labeled complementary strand of a cloned single-stranded DNA is synthesized utilizing an oligonucleotide primer to initiate synthesis and dideoxynucleotides to randomly terminate synthesis. The primer, which anneals to a primer binding site of vector DNA flanking the DNA to be sequenced, is extended by a DNA polymerase in the presence of labeled and unlabeled deoxynucleoside triphosphates. The resulting reaction products, which include a distribution of DNA fragments having primer-defined 5'termini and differing dideoxynucleotides at the 3'termini, are then separated by gel electrophoresis and the base sequence of the fragments are identified.

While numerous modifications and improvements to the strategies referred to above have been developed, most sequencing techniques require the presence of a known primer binding site for every 300 to 500 nucleotides to be sequenced either, for example, for initiation of DNA synthesis or for hybridization to different length DNA fragments having a common end. However, as such approaches utilize a "ladder" of DNA fragments containing the primer binding site (or its complement), the amount of sequence information that can be obtained is limited by the present inability to resolve DNA fragments greater than 500 nucleotides in length on sequencing gels.

Accordingly, methodology described by Guo and Wu, *Nucleic Acids Res.*, 10:2065 (1982); and *Meth. Enz.*, 100:60 (1983), which is not dependent upon primer binding sites, is highly desirable for sequencing DNA greater than 500 nucleotides. This method involves partially digesting linear double stranded DNA with *E. coli* exonuclease III to produce DNA fragments with 3' ends shortened to varying lengths, performing the dideoxy primer extension reactions of Sanger, supra, with the shortened 3' ends as primers for DNA synthesis, and digesting the DNA with a selected restriction enzyme that cleaves near one end of the molecule adjacent to, but not within, the labeled region of DNA. By digestion of the DNA with a selected restriction enzyme, the labeled DNA strands from one end of the molecule are made small enough to be resolved on a sequencing gel. Each successive deletion in length, therefore, brings "new" regions of the target DNA into sequencing range.

However, certain disadvantages inherent in the methodology of Guo and Wu, supra, limit its usefulness for the large scale sequencing of DNA. For example, this approach depends upon the selection of appropriate restriction enzymes which cleave at restriction sites in close proximity to particular *E. coli* exonuclease III endpoints, but not within the labeled DNA as this would result in two or more superimposed sequence ladders. The selection of appropriate restriction enzymes generally requires, therefore, the restriction mapping of DNA fragments to identify sites in close proximity to the numerous exonuclease III endpoints. However, the determination of restriction maps tends to be both time consuming and labor intensive. Specifically, restriction mapping to the resolution needed for DNA sequencing involves the digestion of each region of DNA with combinations of 20 or more enzymes to uncover the relative position of restriction sites. This may require over 100 enzymatic reactions followed by numerous electrophoretic separations. Further, significant amounts of DNA are consumed in the mapping process and interpretation of the data generally requires a substantial amount of time.

In addition to the foregoing limitations inherent in current sequencing techniques, the generation of DNA substrate molecules for each 300 to 500 nucleotides to be sequenced is presently required. Assuming no overlapping sequence between substrate molecules, the sequencing of both strands of an entire mammalian genome would, therefore, require the generation of at least 20 million DNA substrate molecules.

A non-ordered approach to sequencing, e.g., shotgun sequencing, would require the generation of 100 to 200 million DNA templates. Although there has been effort directed to automating the steps presently involved in DNA substrate generation, e.g., restriction mapping, preparation of subfragments for subcloning, identification of subclones, growing bacterial cultures, and purifying nucleic acids, it is unlikely that human intervention can be substantially eliminated from the process. Current approaches, therefore, are less than optimal for the large scale sequencing of DNA, particularly sequencing the human genome.

Although the problems enumerated above are not intended to be exhaustive, the limitations inherent in methods presently available for sequencing DNA are readily apparent. Accordingly, there exists a need for an improved method of sequencing DNA that circumvents the need for primer binding sites as well as the need to determine restriction maps. Additionally, there exists a need for an improved method which extends the amount of sequence information obtainable from a DNA substrate, thus substantially reducing the number of DNA substrate molecules required to sequence a given region of DNA. The present invention meets these needs.

SUMMARY OF THE INVENTION

The present invention provides an improved method of determining the nucleotide base sequence of DNA. The method of the invention involves the preparation of a DNA substrate comprising at a set of molecules, each having a template strand and a primer strand, wherein the 3' ends of the primer strands of the molecules terminate at about the same nucleotide position on the template strands of the molecules within each set. Preferably, the template and primer strands of the molecules are of unequal lengths wherein the 3' ends of the primer strands of the molecules terminate at about the same nucleotide position on the template strands of the molecules within each set. DNA synthesis is induced to obtain labeled reaction products comprising newly sythesized DNA complementary to the template strands using the 3' ends of the primer strands to prime DNA synthesis, labeled nucleoside triphosphates, at least one modified nucleoside triphosphate, and preferably, a suitable chain terminator, wherein the modified nucleoside triphosphate is selected to substantially protect newly synthesized DNA from cleavage. Thereafter, the labeled reaction products are cleaved at one or more selected sines to obtain labeled DNA fragments wherein newly synthesized DNA is substantially protected from cleavage by the incorporation of the modified nucleotide. The labeled DNA fragments obtained in the preceding step are separated and their nucleotide base sequence is identified by suitable means. The advantages of the present invention over prior art methods will become apparent after consideration of the accompanying drawings and the following detailed description of the invention.

BRIEF DESCRIPTION OF THE DRAWINGS

FIG. 3 provides a schematic representation of labeled chain terminated reaction products prepared in accordance with a preferred embodiment of the invention. A hypothetical template strand and primer strand of DNA substrate molecules, generated by exonuclease deletions at various time points, are shown. The bold sequence represents DNA synthesized during primer extension reactions, i.e., newly synthesized DNA, in the presence of the modified deoxynucleoside triphosphate 5-methyl dCTP, labeled nucleoside triphosphates, and dideoxynucleoside triphosphates to selectively terminate DNA synthesis. The incorporation of the modified nucleotide 5-methyl dCMP in the newly synthesized DNA is designated by an asterisk.

FIG. 4 illustrates schematically, for a hypothetical template:primer combination, the effects of digesting labeled reaction products prepared in accordance with a preferred embodiment of the invention with the restriction enzyme Nci I. The bold sequence represents newly synthesized DNA and the incorporation of the modified nucleotide 5-methyl dCMP in the newly synthesized DNA is designated by an asterisk. As shown in this figure, the newly synthesized DNA, i.e., labeled DNA incorporating the modified nucleotide 5-methyl dCMP, is protected from restriction enzyme digestion. Cleavage of the unlabeled DNA of the labeled reaction products is dependent upon the extent of exo III deletion and subsequent 5-methyl dCMP incorporation at various time points.

DETAILED DESCRIPTION OF THE INVENTION

Definitions

Nucleotide

Figure 1:
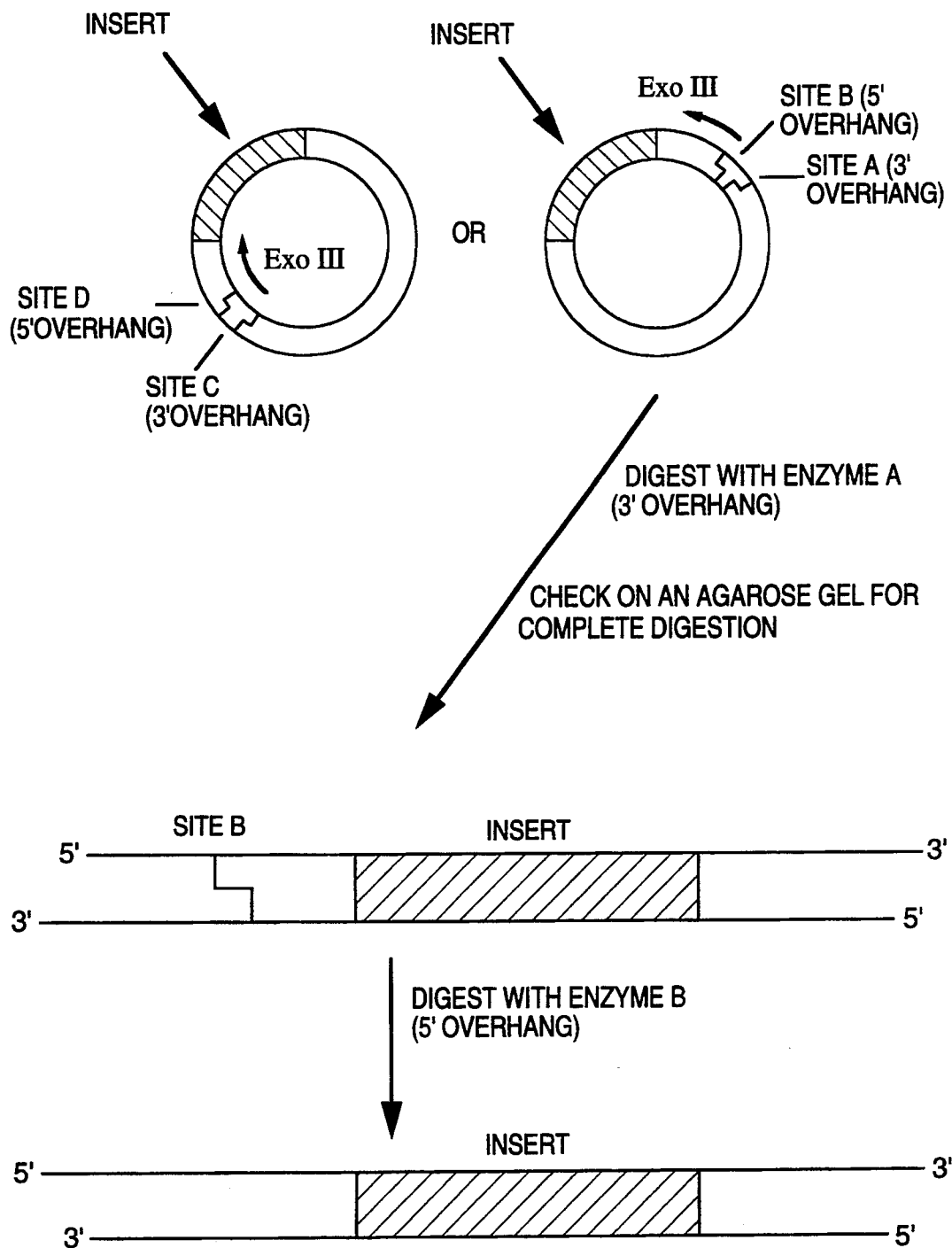
FIG. 1 is a diagrammatic representation of various steps in a preferred embodiment of the invention to prepare linear double stranded DNA for purposes of generating DNA substrate molecules. The shaded area is representative of the DNA to be sequenced and the non-shaded area is representative of vector DNA. First and second restriction sites of the vector are shown as sites A and B, respectively, and sites C and D, respectively.

A monomeric unit of DNA consisting of a sugar moiety (pentose), a phosphate, and a nitrogenous heterocyclic base, i.e., adenosine, thymidine, cytosine or guanosine. The combination of the base and the sugar, in which the base is linked to the sugar moiety via the glycosidic carbon (1' carbon of the penrose), will be referred to herein as a "nucleoside". A nucleoside containing a phosphate group bound to the 3' or 5' position of the pentose will be referred to herein as a "nucleotide". A sequence of operatively linked nucleotides is typically referred to, and referred to herein, as a "base sequence" or "nucleotide sequence", and is represented herein by a left to right orientation in the conventional direction of 5' terminus to 3'-terminus.

Modified Nucleotide

An analog of one of the naturally occurring nucleoside monophosphates, i.e., dAMP, dCMP, dGMP and dTMP, which is incorporated into a nucleic acid. An analog of one of nucleoside triphosphates, i.e., dATP, dCTP, dGTP and dTTP, including an analog that does not have a triphosphate moiety, to be incorporated during synthesis of a nucleic acid will be referred to herein as a "modified nucleoside triphosphate".

Nucleic Acid

A class of molecules that includes ribonucleic acid (RNA), deoxynucleic acid (DNA) in its single or double stranded forms, and polynucleotides.

Primer

A nucleic acid molecule comprising a polymeric unit of DNA and/or RNA having a sequence of operatively linked nucleotides that form a strand of nucleotides capable of acting as a point of initiation of nucleic acid synthesis when placed under conditions in which synthesis of a primer extension product complementary to a template molecule is induced.

Substrate

A nucleic acid molecule comprising a primer strand and a template strand hybridized so as to be capable of permitting the synthesis of a nucleic acid molecule complementary to the template strand. Each strand of the substrate may act as the primer strand and the template strand simultaneously.

Template

A nucleic acid molecule comprising a polymeric unit of DNA or RNA having a sequence of operatively linked nucleotides suitable to provide the genetic information for nucleic acid synthesis such that the genetic information of a newly synthesized strand is complementary to the template strand.

As indicated above, the present invention provides an improved method of determining the nucleotide base sequence of DNA. For purposes of the present disclosure, the term "DNA" is intended to encompass nucleic acid molecules generally. Additionally, those skilled in the art will appreciate that the improved method disclosed herein is broadly applicable to nucleic acids, including deoxynucleic acid (DNA) in its single or double stranded forms, ribonucleic acid (RNA), and polynucleotides.

In accordance with the invention, a DNA substrate comprising a set of molecules is generated, each molecule having a template strand and a primer strand, wherein the 3' ends of the primer strands terminate at about the same nucleotide position on the template strands of the molecules within each set. Preferably, the template strands and the primer strands are of unequal lengths wherein the 3' ends of the primer strands of the molecules terminate at about the same nucleotide position on the template strands of the molecules within each set. DNA substrate molecules for use in the invention are, therefore, partially single stranded and partially double stranded with the 3' ends of the primer strands being recessed. DNA synthesis is induced to obtain labeled reaction products comprising newly synthesized DNA complementary to the template strands using the 3' ends of the primer strands to prime DNA synthesis, labeled nucleoside triphosphates, and at least one modified nucleoside triphosphate. Preferably, a suitable chain terminator, e.g., a dideoxynucleoside triphosphate, is incorporated to produce a labeled chain terminated reaction product. The modified nucleoside triphosphate selected for use, in accordance with the invention, is capable of substantially protecting newly synthesized DNA, i.e., the labeled portion of the labeled reaction products strands in which the modified nucleotide is incorporated, from cleavage. Thereafter, the labeled reaction products are cleaved at one or more selected sites by a suitable reagent to obtain labeled DNA fragments wherein newly synthesized DNA is substantially protected from cleavage by the incorporation of the modified nucleotide. Preferably, the labeled reaction products have the same 5' ends and differing 3' ends resulting from the incorporation of a suitable chain terminator during the preceding step.

Additionally, as used herein, the term "site" refers to a site which is specifically cleaved by a restriction endonuclease or other site specific reagent, including, for example, an oligonucleotide coupled to cleaving moieties. The labeled DNA fragments obtained by cleavage at one or more specific sites are then separated according to their lengths, for example, by standard gel electrophoresis techniques, and their nucleotide sequence is identified by suitable means to yield sequence information adjacent to the 3' endpoints of the original primer strands within each set of DNA substrate molecules.

Generation of DNA Substrate

The generation of a DNA substrate for use in the invention is preferably accomplished by exposing double stranded DNA molecules to a suitable exonuclease capable of deleting DNA from one or both 3' ends of the double stranded DNA in a 3' to 5' direction, e.g., *E. coli* exonuclease III, to produce DNA molecules having at least one strand with a 3' recessed end. See, Guo and Wu, *Nucleic Acids Res.*, 10:2065 (1982); and *Meth. Enz.*, 100:60 (1983), both incorporated by reference herein. Preferably, the double stranded DNA molecules are exposed to the exonuclease for times and under conditions sufficient to produce differing sets of molecules having strands of varying lengths. *E. coli* exonuclease III is particularly preferred for use in the invention as it is capable of deleting a substantially uniform number of nucleotides from each set of DNA substrate molecules as a function of time.

Figure 2:
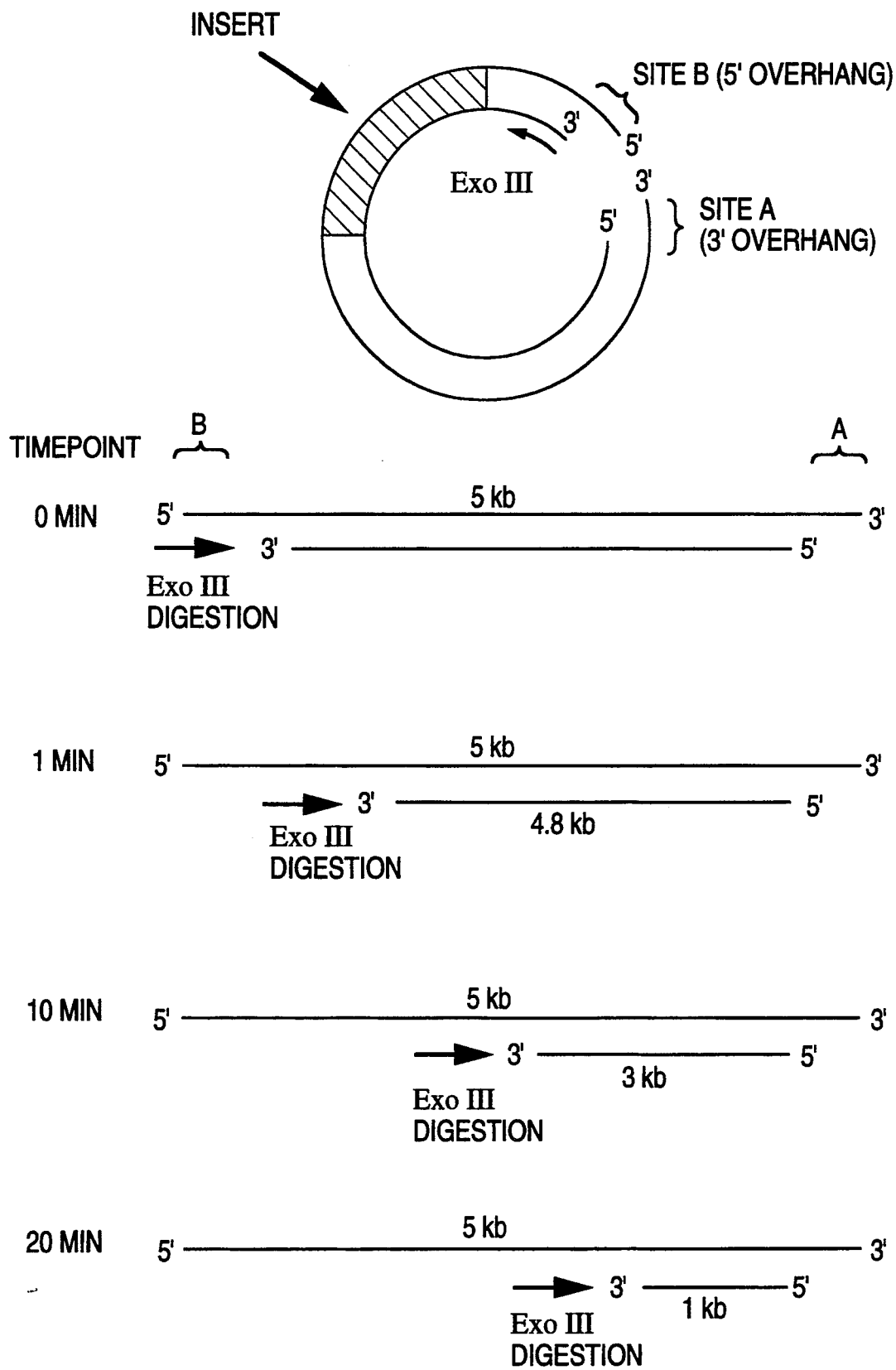
FIG. 2 illustrates schematically various steps in a preferred embodiment of the invention to generate DNA substrate molecules by subjecting linear double stranded DNA to E. coli exonuclease III digestion for increasing time intervals.

In a preferred embodiment of the invention, a DNA substrate is generated by inserting double stranded DNA into a vector, e.g., a plasmid, cosmid, phagemid, or a phage derived vector, comprising first and second restriction sites on at least one side of the DNA insert such that the vector can be cleaved to produce a linear double stranded DNA molecule with the DNA insert at one end of the molecule and the vector sequence at the other end. Vectors suitable for use in the invention, comprising first and second restriction sites on at least one side of the DNA insert wherein the first restriction site is adjacent to the second restriction site and distal to the DNA insert, are shown in FIG. 1. Such vectors are commercially available and can be constructed by standard techniques. Preferably, the occurrence of the first and second restriction sites in the vector is rare or unique, i.e., restriction sites comprising a recognition sequence of at least six nucleotides, and particularly, at least eight nucleotides, e.g., a Not I restriction site. The first restriction site is, preferably, cleaved by a first restriction endonuclease selected to leave a 3' overhang which is not susceptible to exonuclease digestion. Alternatively, however, the first restriction site can be cleaved by a first restriction endonuclease selected to leave a 5' overhang and thionucleotides capable of protecting against exonuclease digestion, can be incorporated by a DNA polymerase. See, Guo and Wu, supra. The second restriction site is cleaved by a second restriction endonuclease selected to leave a 5' overhang or blunt end, both of which are susceptible to exonuclease digestion, at the end of the linear double stranded DNA molecule having the DNA insert. The linear double stranded DNA is then subjected to digestion with an exonuclease capable of digesting the 3' strand of the double stranded DNA in a 3' to 5' direction for times and under conditions sufficient to produce differing sets of molecules having strands of varying lengths. FIG. 2 illustrates the effect of exonuclease digestion on linear double stranded DNA after increasing time intervals. The sets of DNA molecules produced at each time point have strands deleted about the same number of nucleotides whereas the sets of DNA molecules produced at different time points have strands deleted a substantially different number of nucleotides. Each set of DNA substrate molecules will, therefore, have two strands of unequal lengths wherein the 3' ends of the shorter strands terminate at about the same nucleotide position on the longer strands of the molecules.

In an alternative preferred embodiment of the invention, a DNA substrate is generated by inserting a DNA sequence into a vector, e.g., a plasmid, cosmid, phagemid, or phage derived vector, comprising a first restriction site capable of being cleaved by a first restriction endonuclease such that a linear double stranded DNA molecule is produced with the DNA insert at one end of the molecule and the vector sequence at the other end. The first restriction endonuclease is further selected to cleave the first restriction site such that both ends of the resulting linear double stranded DNA molecule are susceptible to digestion by a 3' exonuclease, preferably E. coli exonuclease III. The first restriction site is preferably located in close proximity to the vector:DNA insert junction, i.e., less than 500 nucleotides and, preferably, less than 100 nucleotides from the vector:insert junction. Additionally, it is preferable that the occurrence of the first restriction site in the vector is rare or unique, i.e., a restriction site comprising a recognition sequence of at least six nucleotides, and particularly, at least eight nucleotides, e.g., a Not I restriction site. Vectors useful in this embodiment of the invention are substantially incapable of being cleaved at the selected site or sites at which the labeled reaction products, produced as described herein, are cleaved to obtain labeled DNA fragments for sequence determination. For example, this embodiment of the invention contemplates the selection of vectors that lack one or more normally common restriction sites. Such vectors are commercially available and can be constructed by standard techniques. Alternatively, however, it will be recognized that vectors containing restriction sites capable of being substantially protected from cleavage by a site specific reagent can be employed in this embodiment of the invention. The linear double stranded DNA molecule is thereafter subjected to digestion with an exonuclease capable of digesting the 3' ends of both strands of the molecule in a 3' to 5' direction for times and under conditions sufficient to produce differing sets of molecules having strands of varying lengths. The sets of DNA molecules produced at each time point have strands deleted about the same number of nucleotides whereas the sets of DNA molecules produced at different time points have strands deleted a substantially different number of nucleotides. The molecules within each set will, therefore, have two strands of approximately equal lengths wherein the 3' ends of the strands terminate at about the same nucleotide position on the opposite strands of the molecules.

In an alternative embodiment of the invention, a DNA substrate is generated by inserting double stranded DNA into a vector comprising at least one selected recognition sequence derived from a suitable bacteriophage, e.g., an fl or phi X bacteriophage, and nicking one strand of the double stranded vector DNA with an enzyme capable of recognizing and nicking the selected recognition sequence, e.g., the gene II protein derived from an fl bacteriophage or gene A protein derived from a phi X bacteriophage. See, Dotto et al., J. Mol. Biol., 162:335 (1982); Horiuchi, J. Mol. Biol., 188:215-223 (1986); Baas et al., J. Mol. Biol., 102:633-656 (1976); and Sanger et al., Nature, 265: 687-695 (1977). The single strand nick provides a site of entry for a suitable exonuclease, e.g., E. coli exonuclease III. The 3' end of the nicked strand permits exonuclease digestion, from the 3' end to the 5' end of the nicked strand, to produce a gapped duplex. Preferably, the exonuclease deletions proceed for times and under conditions sufficient to produce differing sets of molecules having circular single strands, i.e., gapped duplexes, of varying lengths. Vectors comprising recognition sequences derived from the fl and phi X bacteriophages are commercially available and can be constructed by standard techniques. The gene II and gene A proteins can be obtained as described by Greenstein and Horiuchi, J. Mol. Biol., 197: 154-174 (1987); and Langeveld et al., FEBS Letters, Vol. 114, No.2:269-272 (1980).

In certain applications of the invention it may be desirable to generate DNA substrate molecules with polymerase chain reaction amplified DNA products. The polymerase chain reaction ("PCR") is well known in the art and described in U.S. Pat. Nos. 4,683,202 and 4,683,195. Embodiments of the invention that contemplate the use of PCR amplified DNA products involve the selection of first and second PCR amplification primers wherein either or both of the first and second primers are capable of substantially blocking exonuclease digestion from one end of the double stranded PCR amplified DNA product. For example, either or both of the first and second primers can contain one or more restriction sites capable of substantially blocking exonuclease activity, e.g., a restriction site leaving a 3' overhang after restriction enzyme digestion. However, it will be understood that only the first or second primer will be used to protect the double stranded PCR amplified DNA product from exonuclease digestion at one time. The first and second primers can both be selected to hybridize to the DNA to be sequenced, or either or both of the first and second primers can be selected to hybridize to a vector sequence proximal to a site in which the DNA to be sequenced has been inserted. See, Lew and Kemp, Nucleic Acids. Res., 17:5859-5860 (1989); and Jansen et al., Genomics, 4:198-205 (1989). Alternatively, however, the vector sequence between the primer binding site and the DNA insert can contain restriction sites capable of substantially blocking exonuclease digestion from one end of the molecule. Accordingly, DNA substrate molecules suitable for use in the invention can be generated from PCR amplified DNA products susceptible to exonuclease digestion from one end of the double stranded molecule, e.g., the undigested blunt end.

In a further alternative embodiment of the invention, single stranded DNA molecules can be employed to generate DNA substrate molecules having strands of varying lengths, for example, by permitting a suitable DNA polymerase, in the presence of a suitable primer and nucleoside triphosphates, to synthesize DNA complementary to the single stranded DNA. The single stranded DNA is preferably contacted with the DNA polymerase for times and under conditions sufficient to produce differing sets of molecules having strands of varying lengths. Additionally, it will be recognized that this approach can also be suitably utilized with double stranded DNA molecules by first removing one strand by techniques well known in the art.

Additionally, it will be recognized that DNA substrate molecules for use in the invention can be prepared by various alternative approaches provided that the molecules are partially single stranded and partially double stranded with the 3' ends of the primer strands being recessed. For example, a suitable DNA substrate can be prepared using naturally occurring double stranded linear DNA, or synthetic double stranded DNA (cDNA), and an enzyme to substantially block either exonuclease or DNA polymerase activity at one end of the double stranded DNA molecule. Further, DNA binding proteins, selected to substantially block either exonuclease or DNA polymerase activity, can be utilized for purposes of diminishing the range of exonuclease or polymerase activity for each respective time point. See, Wu, *Nature*, 317:84–87 (1985).

Synthesis Reactions—Labeled Reaction Products

The primer strands of the DNA substrate molecules, generated as described above are used to induce DNA synthesis, preferably in four parallel sequencing reactions, to obtain labeled reaction products. In accordance with the invention, at least one modified nucleoside triphosphate, selected to substantially protect newly synthesized DNA from cleavage by at least one reagent, is substituted for one of the four normally occurring nucleoside triphosphates, i.e., dATP, dCTP, dGTP and dTTP, during the synthesis reactions. Further, the newly synthesized DNA is labeled during the synthesis reactions such that labeled DNA fragments containing newly synthesized DNA can be distinguished from DNA fragments that do not contain newly synthesized DNA. The labeling of the newly synthesized DNA can occur by incorporation of one or more labeled nucleotides, or labeled modified nucleotides, in newly synthesized DNA. In the context of the invention, the term "newly synthesized DNA" refers to DNA synthesized during a primer-induced synthesis reaction, capable of providing nucleotide sequence information of the template strand and/or the complement of the template strand, and into which at least one modified nucleotide is incorporated. The present invention is broadly applicable to DNA sequencing strategies based upon the well known enzymatic methods of Sanger, as well as the chemical methods of Maxam-Gilbert, provided that at least one modified nucleotide is incorporated in newly synthesized DNA of the labeled reaction products and that labeled DNA fragments containing newly synthesized DNA can be distinguished from DNA fragments that do not contain newly synthesized DNA.

Preferably, the enzymatic or dideoxynucleotide sequencing approach of Sanger et al., *Proc. Natl. Acad. Sci.*, 74:5463 (1977), incorporated by reference herein, or one of the many prior art modifications or improvements to the Sanger methodology, is relied upon to produce labeled reaction products in accordance with the invention. Accordingly, dideoxynucleoside triphosphates are used in the presence of at least one modified nucleoside triphosphate, preferably in four parallel primer extension reactions, to selectively terminate DNA synthesis at specific nucleotides. However, one reaction, incorporating four different dideoxynucleoside triphosphates that are each uniquely labeled, may be used to generate labeled reaction products terminating at specific nucleotides. See, Prober et al., *Res. Articles*, 238:336 (1987). FIG. 3 provides a schematic representation of the labeled reaction products resulting from dideoxy chain termination reactions in accordance with the invention. By cleaving the labeled reaction products, separating labeled DNA fragments and correlating the particular dideoxynucleotide responsible for terminating synthesis with the lengths of labeled DNA fragments, the sequence of newly synthesized DNA (and thereby the template) can be determined.

Additionally, the present invention is applicable to the chemical degradation approach of Maxam and Gilbert, *Meth. Enz.*, 65:499 (1977), incorporated by reference herein. For purposes of the invention, the labeling of DNA is performed in an initial step during which a short stretch of labeled DNA (about 20 to about 40 nucleotides) is synthesized in the presence of at least one modified nucleoside triphosphate. Typically, such short labeling reactions are controlled by performing the labeling synthesis reaction with a limiting amount of one or more of the nucleoside triphosphates. After the labeling reaction "stalls", the synthesis reaction is permitted to continue in the presence of at least one modified nucleoside triphosphate but without labeled nucleoside triphosphates. The labeled reaction products are then cleaved sequentially by restriction enzyme digestion (with an enzyme substantially inhibited by the modified nucleotide) and chemical degradation reactions, as described by Maxam and Gilbert, supra, to permit nucleotide sequence determination.

Alternatively, the present invention is applicable to a sequencing strategy that utilizes "weak link" nucleotides capable of rendering the newly synthesized DNA more susceptible to cleavage by a suitable reagent, e.g., an alkylating reagent. See, Gish and Eckstein, *Science*, 240:1520 (1988); and Nakamaye et al., *Nucleic Acids Res.*, 16:9947–9950 (1988), incorporated by reference herein. In this approach, a nucleoside alpha-thio-triphosphate is added in small quantities to each synthesis reaction for purposes of creating a "weak link" in the nucleotide chain. DNA synthesis involving short labeling reactions, followed by unlabeled synthesis reactions, are performed as described above. The labeled reaction products are thereafter cleaved sequentially by restriction enzyme digestion and by exposure to an alkylating agent, e.g., iodoethanol, to cleave the labeled reaction products at phosphorothioate bonds. The labeled DNA fragments produced may thereafter be physically separated to yield sequence information.

Modified nucleoside triphosphates suitable for use in the invention are analogs of the normally occurring nucleoside triphosphates, i.e., dATP, dCTP, dGTP and dTTP, capable of being incorporated into double stranded DNA as nucleoside monophosphate analogs, i.e., nucleotide analogs, during chain extension. For example, the modified nucleoside triphosphate 5-methyl-deoxycytosine-5'-triphosphate (5-methyl dCTP), will be incorporated into newly synthesized DNA as the modified nucleotide 5-methyl-deoxycytosine-5'-monophosphate (5-methyl dCMP) at positions complementary to guanosine in the template strand but not at positions complementary to adenosine, cytosine or thymidine.

Modified nucleoside triphosphates selected for use in the invention are capable of substantially protecting newly synthesized DNA of the labeled reaction produces from cleavage by at least one reagent, e.g., a restriction endonuclease or chemical reagent, under conditions to cleave or substantially cleave unmodified DNA. As used herein, the term "restriction endonuclease" includes restriction enzymes, restriction endonucleases and other site specific endonucleases or reagents capable of cleaving or substantially cleaving DNA at or near a specific nucleotide sequence. Accordingly, the terms "restriction endonuclease" and "restriction enzyme" are used interchangeably herein.

Modified nucleoside triphosphates preferred for use in the invention are methyl deoxynucleoside triphosphates. Particularly preferred for use are 5-methyl-deoxycytosine-5'-triphosphate (5-methyl dCTP) and 7-methyl-deoxyadenosine5'-triphosphate (7-methyl dATP). Also preferred for use are alpha-thio-deoxynucleoside triphosphates. However, the present invention contemplates the use of a multitude of possible modified nucleoside triphosphates. Accordingly, those skilled in the art having the benefit of this disclosure will appreciate that alternative modified nucleoside triphosphates capable of being incorporated into newly synthesized DNA of the labeled reaction products as a modified nucleotide, and substantially protecting newly synthesized DNA from cleavage, may be suitably utilized in the invention.

For purposes of the present invention, the modified nucleotide "substantially protects" newly synthesized DNA of the labeled reaction products if the rate of cleavage of newly synthesized DNA by a selected reagent, e.g., a restriction enzyme, is at least about ten fold less, and preferably fifty fold less, than the rate of cleavage of DNA in which the modified nucleotide is not incorporated. It will be appreciated, however, that complete protection of newly synthesized DNA is not required to interpret nucleotide sequence information from cleavage products provided that the labeled DNA fragments that are partially cleaved by the selected reagent represent an insignificant portion of all labeled DNA fragments. Accordingly, the substantial protection provided by the present invention permits desired labeled DNA fragments to be detected without a significant level of background.

Modified nucleoside triphosphates suitable for use in the present invention are available commercially and can be prepared synthetically or by chemical modification of nucleoside triphosphates by techniques well known in the art. Alternatively, modified nucleoside triphosphates can be isolated from natural sources by standard techniques, e.g., 5-methyl-deoxycytosine-5'-monophosphate can be isolated from mammalian chromosomal DNA.

A determination of the suitablility of modified nucleoside triphosphates for use in the present invention can be accomplished by conventional techniques well known in the art. For example, standard gel electrophoresis of primer extension products can be relied upon to determine whether particular modified nucleotides are incorporated during DNA synthesis. In addition, restriction digestion of the primer extension products by standard procedures can be used to determine if DNA synthesized with desired modified nucleoside triphosphates is substantially protected from cleavage at restriction sites in which the modified nucleotide is incorporated. Similarly, the suitability of specific modified nucleoside triphosphates with a desired DNA synthesis inducing agent, e.g., a DNA polymerase, may be determined by standard primer extension assays that determine the kinetics of the incorporation of the modified nucleotide in comparison to naturally occurring nucleotides.

The labeled nucleoside triphosphates suitable for use in the invention, i.e., nucleoside triphosphates that are linked to molecules capable of either directly or indirectly producing a detectable signal, may be provided with the same labels used in prior art methods for determination of the nucleotide base sequence of DNA. Among such suitable labels for use in the invention are radioactive, fluorescent, and biotinylated labels, all of which are well known in the art. Radioactive labels, for example, alpha-$^{32}$P labeled or $^{35}$S labeled nucleoside triphosphates can be suitably utilized and are commercially available. However, in certain applications of the invention fluorescently labeled nucleoside triphosphates, as described by Prober et al., *Res. Articles,* 238:336 (1987), and available commercially, or biotinylated nucleoside triphosphates, as described by Richterich, et al., *Res. Report,* 7:52 (1982), and available commercially, may be desirable. Additionally, the modified nucleoside triphosphates selected for use in the invention may provide the source of the label.

Suitable chain terminator agents for use in preferred embodiments of the invention, for example, 2',3'-dideoxynucleoside triphosphates, are well known in the art and are commercially available. As previously indicated, the incorporation of a dideoxynucleotide at the 3' end of the labeled chain terminated reaction products permits the termination of DNA extension selectively at one of the four nucleotide bases. In each of the four parallel reactions performed in accordance with preferred embodiments of the invention, one of the four 2'3'-dideoxynucleoside triphosphates are utilized as described by Sanger et al., supra. Alternatively, however, the chain terminator may be the labeled nucleoside triphosphate selected for use in the invention. See, Prober et al., supra. Accordingly, each of the labeled chain terminated reaction products will have a fixed 5' end and a variable 3' end terminating at a specific base.

Further in accordance with the invention, an appropriate agent is utilized for inducing or catalyzing the chain extension reaction, which is permitted to occur under conditions well known in the art. The inducing agent may be any agent capable of accomplishing the synthesis of the labeled reaction products, and preferably, labeled chain terminated reaction products. Suitable enzymes for this purpose include, for example, Klenow fragment of *E. coli* DNA polymerase I, Taq DNA polymerase, T7 DNA polymerase, reverse tranascriptase, and other enzymes which will facilitate the combination of nucleoside triphosphates, particularly the modified nucleoside triphosphate selected for use in the invention, such that newly synthesized DNA of the labeled reaction products is complementary or substantially complementary to the template strand. Additionally, it will be appreciated that the inducing agent may be a suitable RNA polymerase in certain applications of the invention.

Cleavage of Labeled Reaction Products

In accordance with the invention, the labeled reaction products are cleaved with a reagent, preferably a restriction endonuclease, at a selected site or sites to obtain labeled DNA fragments wherein newly synthesized DNA is substantially protected from cleavage by the incorporation of the modified nucleotide selected for use as described herein. Such labeled DNA fragments are truncated at one or more specific sites without cleaving within the labeled region, i.e., the newly synthesized DNA. Preferably, the truncated labeled DNA fragments all share the same 5' end and have differing 3' ends created by the incorporation of dideoxynucleotides during the primer extension reaction. Such labeled DNA fragments can thereafter be separated by standard gel electrophoresis to yield sequence information adjacent to the 3' endpoints of the original primer strands of the DNA substrate molecules. FIG. 4 illustrates schematically the effect of restriction enzyme digestion of the labeled reaction products to produce labeled DNA fragments.

Reagents generally preferred for use in the invention are frequently cutting restriction endonucleases having a four or five nucleotide recognition sequence, and therefore, digesting the labeled reaction products approximately once every 250 to 500 nucleotides. This permits the labeled reaction products to be truncated to a size that, on average, will be small enough to be resolved on a standard acrylamide sequencing gel. It will be recognized that the selected reagent may cleave the labeled reaction products at a site or sites remote from newly synthesized DNA, i.e., the labeled region of the DNA, producing labeled DNA fragments that are too large to resolve on a standard sequencing gel. Additionally, it will be recognized that the selected reagent may cleave the labeled reaction products at a site or sites too close to the labeled region. Under such circumstances, it is possible to obtain two or more sets of labeled DNA fragments representing two or more different sequences. However, the cleavage frequency of the specific reagent can be selected to minimize the occurrence of such events, yielding useful sequence information a substantial portion of the time.

Particularly preferred for use in the invention are those frequently cutting restriction endonucleases which are substantially inhibited from cleaving DNA modified by the incorporation of 5-methyl-dCMP. Enzymes suitable for this purpose are provided in Table I herein. Particularly preferred for use are the restriction endonucleases Sau 3A, Dde I and Nci I. However, it will be appreciated by those skilled in the art that alternative restriction endonucleases and reagents, including chemical reagents, may be selected to cleave the labeled reaction products to obtain labeled DNA fragments as described herein provided that such reagents are substantially inhibited from digesting newly synthesized DNA.

TABLE I

| Restriction Enzymes | |
|---|---|
| Acc I | Hpa II |
| Ava II | Hph I |
| Bal I | Nar I |
| BamH I | Nci I |
| Ban II | Not I |
| Bsp1286 I | Pst I |
| BstX I | Pvu II |
| Dde I | Sac I |
| EcoR II | Sau3A I |
| Hae II | Sau96 I |
| Hae III | ScrF I |
| HgiA I | Sma I |
| Hind III | Xho I |

Additionally, it will be understood by those skilled in the art that certain reagents, particularly restriction endonucleases, may recognize degenerate populations of nucleotide sequences. Accordingly, the present invention contemplates the selection of reagents which are substantially inhibited from cleaving newly synthesized DNA at substantially all recognition sequences comprising a degenerate population of nucleotide recognition sequences. Further, as indicated above, a preferred embodiment of the invention contemplates the selection of a reagent, preferably a restriction endonuclease, that is substantially incapable of cleaving vector DNA into which the DNA to be sequenced has been inserted.

Separation of Labeled DNA Fragments

As indicated above, the labeled DNA fragments are separated according to their lengths by standard gel electrophoresis. It will be understood that the method of separation and detection of the labeled DNA fragments will be dependent upon the method of labeling DNA. For example, if the labeled DNA is radioactively labeled, detection of the labeled DNA fragments is accomplished by standard autoradiography or other methods well known in the art to detect emitted particles. Alternatively, if the DNA is fluorescently labeled, detection of the labeled DNA fragments is accomplished as described by Prober et al., supra. However, if the DNA is labeled with an antigen or biotin, detection of the labeled DNA fragments may involve transfer to a solid support followed by binding/color development steps as described by Richterich et al, supra. Thereafter, the nucleotide base sequence of the labeled DNA fragments are analyzed by suitable means well known in the art.

Further in accordance with the present invention, a kit is provided for the determination of the nucleotide base sequence of DNA. The kit comprises a suitable exonuclease capable of deleting DNA from the 3' end of one strand of a double stranded DNA molecule, and at least one modified nucleoside triphosphate selected to substantially protect newly synthesized DNA into which it is incorporated from cleavage. Preferably, the modified nucleoside triphosphate is a methyl deoxynucleoside triphosphate, particularly 5-methyl dCTP. The kit may, however, comprise additional components including, for example, a suitable DNA polymerase, deoxy/dideoxynucleoside triphosphate reaction mixes, restriction enzymes, exonuclease buffers, reaction buffers and an instruction manual.

The present invention overcomes the limitations of prior art methods for determination of the nucleotide base sequence of DNA as it circumvents the need for primer binding sites as well as the need to determine restriction maps. Additionally, the present invention is advantageous, particularly for the large scale sequencing of DNA, as it extends the amount of sequence information that can be obtained from one DNA substrate molecule, thus substantially reducing the number of DNA substrate molecules that are required to sequence a given segment of DNA. Further, the invention permits sequence information to be obtained simultaneously from many regions of the DNA substrate molecules and in an "ordered" approach such that one can return directly to uninformative regions of the DNA for further clarification.

The following example is offered to further illustrate the advantages of the present invention and is not intended to limit the invention in any way. In the example, the nucleotide sequence of an actin cDNA isolated from mouse smooth muscle was determined by the method of the present invention and demonstrated to be homologous to a previously published mouse skeletal muscle actin cDNA sequence as described by Leader et al., *DNA,* 5;235-238 (1986). The only differences observed were a "T" for a "C" at nucleotide position 785 and a "C" for a "T" at nucleotide position 938. While Applicants do no intend to be bound by any theory, it is believed that these nucleotide differences may be attributable to the isolation of the cDNAs from different tissues, or represent silent sequence polymorphisms. Applicants do not believe, however, that these differences represent errors in the sequence as the appropriate complementary nucleotide on the complementary strand was observed.

EXAMPLE I

Preparation of DNA Substrate Molecules

Restriction Digestion of Double Stranded Circular DNA

Approximately 500 $\mu$g of a 4.4 kilobasepair double stranded circular Bluescript SK (−) vector (Stratagene, La Jolla, Calif.) containing an actin cDNA insert, isolated from mouse smooth muscle by standard procedures, was prepared by a standard CsCl/ethidium bromide procedure as described in Ausubel, et al., *"Current Protocols in Molecular Biology"*, John Wiley & Sons, New York (1987), pp 1.7.5–1.7.7. To produce double stranded linear DNA molecules having an entry point for *E. coli* exonuclease III on only one strand of the double stranded DNA, 125 $\mu$g of the DNA was first cut with 250 units of Sac I (Stratagene, La Jolla, Calif.) at 37° C. for 1 hour in 1 X Universal Buffer (100 mM potassium acetate; 25 mM Tris-Cl pH 7.6; 0.5 mM beta-mercaptoethanol; 10 mM magnesium acetate; and 100 $\mu$g/ml bovine serum albumin) in a total reaction volume of 500 microliters. One $\mu$g of the DNA was then applied to a 0.8% agarose gel in 1 X E buffer, electrophoresed, stained with ethidium bromide, and examined under ultraviolet light, Ausubel, et al., supra, to determine that the DNA had been digested to completion. The DNA was then digested by adding 250 units of EcoR (Stratagene, La Jolla, Calif.) to the reaction mixture and incubating at 37° C. for an additional 1 hour. The reaction mixture was then heated to 65° C. for 20 minutes. The DNA was precipitated by adding 2.5 volumes of ethanol and centrifugation was performed at 11,000 g for 30 minutes. The ethanol was decanted and the DNA pellet was washed once with 70% ethanol, lyophilized to removed the excess ethanol, and resuspended in H$_2$O at a concentration of 1 $\mu$g/$\mu$l.

Exonuclease Digestion of Linear Double Stranded DNA

To generate DNA substrate molecules the linear double stranded DNA, prepared as described above, was subjected to exo III (*E. coli* exonuclease III) digestion in exo III buffer (50 mM Tris pH 8, 10 mM MgCl$_2$, 10 mM beta-mercaptoethanol) at a DNA concentration of 200 $\mu$g/ml. One $\mu$g of DNA was removed prior to addition of exo III and saved for subsequent gel analysis. The reaction tube was equilibrated for 5 minutes at 30° C. Twenty units of exo III per $\mu$g of DNA were added and the contents mixed well. Incubation was continued at 30° C. A 25 $\mu$l aliquot (5 $\mu$g of DNA) was removed from the reaction every minute, and each aliquot was made 20 mM in EDTA. The exo III in each aliquot was further inactivated by incubation at 65° C. for 10 min. One $\mu$g (5 $\mu$l) was removed from each time point for alkaline gel analysis as described below. The remaining DNA was extracted with an equal volume of a 50:50 mixture of phenol and chloroform, as described by Ausubel et al., supra, and precipitated with 2.5 volumes of ethanol. The DNA was pelleted by centrifugation as described above and the DNA was resuspended in H$_2$O at a concentration of 0.5 $\mu$g/$\mu$l.

Alkaline Agarose Gel Analysis

To separate the single DNA strands each by size, one $\mu$g of the DNA substrate molecules from each exo III time point was electrophoresed on a vertical, 1.5 mm thick, 0.8% alkaline agarose gel, essentially as described by Maniatis et al., "Molecular Cloning: A Laboratory Manual" Cold Spring Harbor Press, Cold Spring Harbor, N.Y. (1982). The samples were electrophoresed for 18 hours at 20 milliamperes. The gel was stained with ethidium bromide, destained in water, and bands visualized under UV light, as described by Maniatis et al., supra.

Preparation of Labeled Reaction Products

Dideoxy Chain Termination Sequencing Reactions With Modified Deoxynucleoside Triphosphates To prepare labeled reaction products for nucleotide sequence determination the dideoxy chain termination approach, described by Sanger et al., *Proc. Natl. Acad. Sci.,* 74:5463 (1977), was performed with the modified deoxynucleoside triphosphate 5-methyl dCTP (5-methyl-deoxycytosine-5'-triphosphate) (Pharmacia, Piscataway, N.J.) substituted for dCTP. Both reverse transcriptase and T7 DNA polymerase were employed to illustrate that the improved method of the invention is useful with both of these enzymes. For reverse transcriptase reactions, 4 $\mu$g of DNA from each time point were mixed with 4 $\mu$l of alpha-$^{35}$S-dATP (1350 Ci/mmol, 12.5 millicuries/ml (New England Nuclear, Boston, Mass.) and 10 units of avian myeloblastosis virus reverse transcriptase (Stratagene, La Jolla, Calif.) in a total reaction volume of 30 $\mu$l containing 12 mM Tris-Cl pH 8.3, 46 mM NaCl$_2$, and 8.3 mM DTT. Aliquots, 6 $\mu$l each, were immediately added to microfuge tubes containing 4 $\mu$l of the appropriate A, C, G, or T mix: each mix contained 0.5 mM dGTP, dTTP, and 5-methyl-dCTP (Pharmacia, Piscataway, N.J.). The A, C, G, and T mixes also contained respectively 0.001 mM ddATP, 0.25 mM ddCTP, 0,125 mM ddGTP, or 0.5 mM ddTTP (Pharmacia, Piscataway, N.J.). The reaction mixtures were incubated for 20 min at 42° C. Then 2 $\mu$l of chase mix (0.25 mM each dGTP, non-radioactive alpha-thio-dATP, dTTP, and 5-methyl-dCTP) was added to each tube and the mixtures were incubated for an additional 15 min at 42° C., and placed on ice. For the T7 DNA polymerase reactions, 4 $\mu$g of DNA from each time point were incubated with 2 $\mu$l of alpha-$^{35}$S dATP (1350 Ci/mmol, 12.5 millicuries/ml), (New England Nuclear, Boston, Mass.). 4 µl labeling mix (2 µM dGTP, dTTP, and 5-methyl-dCTP), and 6 units of T7 DNA polymerase in a 40 µl total volume containing 28 mM Tris-Cl pH 7.5, 10 mM MgCl$_2$, 35mM NaCl, and 15 mM DTT for 5 min at 22° C. Aliquots, 9 µl each, of this reaction mixture were then added to 5 µl of the A, C, G, and T termination mixes that were prewarmed to 37° C.: each termination mix contained 150 µM non-radioactive alpha-thio-dATP, 5-methyl-dCTP, dGTP, and dTTP. The A, C, G, and T mixes also contained respectively, 15 µM ddATP, ddCTP, ddGTP, or ddTTP. After incubation at 37° C. for 5 min, the tubes were placed on ice.

Selection of Modified Deoxynucleoside Triphosphates

Modified nucleotides were tested to determine the capability of substantially inhibiting restriction enzyme. The effectiveness of modified nucleotides for this purpose, particularly 5-methyl-dCTP, was determined with the following assay. One µg of single stranded M13 mp9 DNA (Pharmacia, Piscataway, N.J.) was placed in 10 µl of water with 14 nanograms of the M13 -20 primer (Pharmacia, Piscataway, N.J.) and incubated at 55° C. for 10 minutes and then at 23° C. for 20 minutes. The modified nucleoside triphosphate to be tested, e.g., 5-methyl dCTP, was substituted for the nucleoside triphosphate for which it is an analog. Numerous components were then added to reach a final volume of 50 µl: the mixture was made 340 µM dGTP, dTTP and either dCTP or 5-methyl-dCTP (dCTP for a control reaction and 5-methyl-dCTP for a test reaction). The reaction was also made 34 µM dATP, and 30 picomoles of alpha-$^{32}$P labeled dATP (800 Ci/mMole) (New England Nuclear, Boston, Mass.) was also added. Five units of the large fragment of $E.$ $coli$ DNA polymerase (Stratagene, La Jolla, Calif.) were added. The reaction was also made 50 mM Tris-Cl pH 7.5, 7 mM MgCl$_2$, and 1 mM dithiothreitol. The reaction was incubated at 23° C. for 1 hour. The reaction was then made 00 mM with NaCl and 2.5 volumes of ethanol were added and the DNA was precipitated as described above. The DNA pellet was dissolved in water at a concentration of 50 micrograms per milliliter. Fifty nanograms of the DNA were then added to water to a volume of 8 µl and the reaction was made 1 X with Universal buffer (see above) to a final volume of 10 µl. Two units of a restriction enzyme to be tested for inhibition were then added and the reaction was incubated at the temperature optimal for the restriction enzyme (typically 37° C.) for one hour. The reaction was then electrophoresed on a 5% acrylamide sequencing gel, as described by Ausubel et al., supra, and the size of the DNA fragments was visualized by autoradiography, as described by Ausubel et al, supra. By comparing the sizes of the DNA fragments between the dCTP and the 5-methyl-dCTP lane, it was determined whether the 5-methyl-dCTP inhibited the restriction enzyme. As the enzyme was inhibited, there were no substantial smaller bands resulting from digestion by the restriction enzyme.

Cleavage of Labeled Reaction Products

Labeled DNA Fragments

After cooling the sequencing reactions on ice, a 7 µl aliquot was frozen for later use and 2-4 units of restriction enzyme BamH I (Stratagene, La Jolla, Calif.) or Sau3A I in other parallel reactions (Stratagene, La Jolla, Calif.), were added directly to the remaining mixture. Restriction enzymes BamH I and Sau3A I are incapable of digesting DNA containing 5-methyl-dCMP at both "C" residues. If necessary for other restriction enzymes, the NaCl concentration may be adjusted to suit the restriction enzyme. Incubation was continued for 45 min at 37° C.

Selection of Restriction Enzymes

To determine the suitability of restriction enzymes for use in the improved method of the invention, the following factors were considered. The recognition sequence of a suitable enzyme is typically 4 to 5 nucleotides in length. Such enzymes will cleave random DNA molecules once every 256 ($4^4$) to once every 1024 ($4^5$) nucleotides. To select the optimum enzyme for cleavage, the concept of the exonuclease III "range" should be considered. At each exo III time point, the lengths of the deleted primer molecules are not identical. If one examines 95% of the molecules, having lengths closest to the average primer size, the difference between the length of the longest primer molecule and the shortest primer molecule within the 95% pool is referred to as the "range" (i.e., the longest 2.5% and the shortest 2.5% of the primers at each time point are not considered). Ideally the enzyme used to cleave the labeled reaction products cleaves random DNA less frequently than I/range. Since the size of the range is proportional to the number of nucleotides deleted by exo III (approximately 15% of the number of nucleotides deleted), enzymes that cleave less frequently for the longer exo III time points are preferable. Additionally, enzymes must also be inhibited by the modified nucleotide being used in the synthesis reactions. Such enzymes can be identified by the primer extension/cleavage assay as described above. To date, we have found 26 enzymes, provided in Table I herein, that are inhibited by 5-methyl-dCMP and are suitable for use in the invention. As a primary enzyme, when no map information is known, we prefer Sau 3A, Dde I, or Nci I since we have obtained reliable sequence information with these enzymes. Nci I cuts less frequently than Sau 3A and Dde I, and is used when the exo III range begins to increase in size.

Separation of Labeled DNA Fragments

Figure 5:
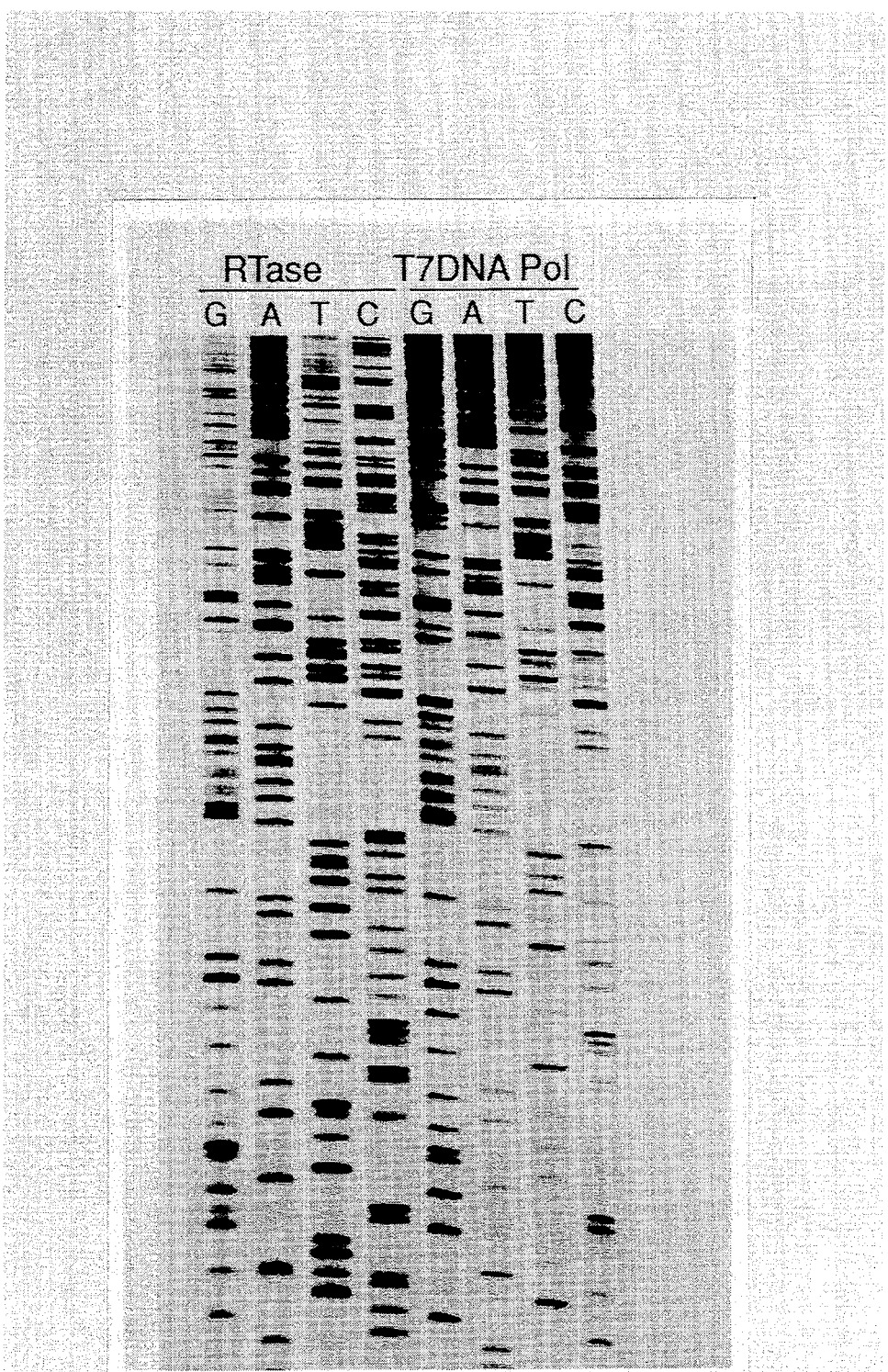
FIG. 5 represents an autoradiogram of sequence ladders, comparing reverse transcriptase and T7 DNA polymerase, for determination of the nucleotide base sequence of DNA in accordance with the improved method of the invention. G, A, T and C represent reactions in which ddGTP, ddATP, ddTTP or ddCTP were used to terminate chain elongation. RTase represents reactions in which reverse transcripase was used to synthesize DNA; T7 DNA Pol represents reactions in which T7 DNA polymerase was used to synthesize DNA.

After completing restriction digestion of the labeled reaction products with BamH I as described above, 7 µl of formamide loading dye was added, samples were heated at 90° C. for 2 minutes, and samples were then cooled on ice for one minute and 3.5 µl was electrophoresed through a 6% acrylamide/urea sequencing gel at 55 Watts, essentially as described by Ausubel et al., supra. The gel was dried, using standard procedures, and exposed to XAR-2 film (Kodak, Rochester, N.Y.) at room temperature overnight. FIG. 5 illustrates the quality of the sequence ladders observed with this method. We have also used the large fragment of DNA polymerase I and Taq DNA polymerase with this method with reasonable success.

It should be noted, however, that the highly interpretable sequence pattern seen in FIG. 5 may not be found under certain circumstances. If the closest cleavage site is greater than 400 nucleotides in the 5' direction of the 3' deleted end of a average length primer, the labeled DNA fragments will be larger than 400 nucleotides and the sequence information will be too large to resolve well with a conventional gel. Alternatively, if the range of exo III deletion endpoints at a given time point encompasses a particular enzyme site, which shall be referred to as site C1, then two populations of labeled DNA strands will be generated. A population of smaller strands will result from digestion by restriction enzyme C at site C1 in the sub-population of molecules that lack methyl-cytosine due to exo III having not proceeded beyond site C1. This population of labeled DNA strands will all share the same 5' end at site C1. Another population of larger labeled strands will result from inhibition of digestion at the C1 sites that have incorporated methyl-cytosine. The common 5' end of such molecules will be created by cleavage at site C2, which shall be considered to be 5' to site C1 on the exo III-deleted primer strand. Since both populations of labeled fragments will be in the same reaction mixture, electrophoresis may yield two superimposed sequence ladders depending on how far restriction enzyme site C2 lies from site C1. If site C2 is N nucleotides from site C1, then fragments from 1 to approximately N-range/2 nucleotides in length, having their 5' end created by cleavage at site C1, will be readable as a single sequence ladder. Fragments greater than approximately N-range/2 nucleotides in length will appear as two superimposed sequences. The superimposed sequences become more prevalent as the size of the exo III range increases. As the size of the range increases, we generally use less frequently digesting enzymes for enzyme C. For example, Nci I digests approximately every 500 nucleotides, and yields fewer superimposed sequence ladders. The disadvantage in using Nci I, however, is that the sequence ladders are frequently in the higher molecular weight region of the gels. Thus, the data must be assessed and less frequent enzymes must be used as the longer exo III time points begin to yield superimposed sequence ladders.

Methods that decrease the size of the exo III range would, of course, be desirable. One such method involves DNA binding proteins to block digestion by exo III. The effect would be to produce a population of DNA substrates in which all of the primer strands were substantially the same length, or effectively reducing the size of the exo III range to zero. By removing the DNA binding protein with a reagent such as phenol, the DNA would then again be susceptible to exo III. Additional exo III digestion would allow the primer strands to be reduced in size again, for varying lengths of exo III incubation, to produce a set of deletions having a much smaller range as compared to the total number of nucleotides deleted.

It should also be noted that even though in the first round of sequencing with a restriction enzyme C chosen from Table I herein not all of the time points may yield substantial stretches of sequence information, the information gained is extremely useful for subsequently obtaining sequence information from the non-informative time points. For example, if sequence information is gained from a 10-minute exo III time point, but no information is gained from an 8minute time point because the closest site C in the 5' direction is greater than 400 nucleotides from the 8-minute 3' endpoints, one can use the sequence information gained from the 10-minute time point to select a new restriction enzyme D more appropriate for the 8-minute time point. In chosing enzyme D from the sequence information that was obtained from the 10-minute time point, one looks for a site closest to the deletion endpoint of the 8-minute time point. One also attempts to chose an enzyme D with a five or six base recognition sequence to decrease the probability that enzyme D will cleave again within the exo III range of the 8-minute deletion endpoints. Moreover, if enzyme D has a six base recognition sequence, its inhibition by methylcytosine is less important since the likelihood of it occurring again within the labeled DNA region is rather insignificant.

Further, a substantial amount of labor can be saved if the original dideoxy reactions are performed with a two or three-fold excess of DNA substrate and the balance of the reaction mixture is frozen after removing an aliquot for digestion with enzyme C. Once some sequence information is obtained and secondary restriction enzymes D, E, F, G, etc. are identified for the secondary sequencing of non-informative time points, the balance of the dideoxy reaction mixtures can be thawed and the appropriate restriction enzyme can be added. After a 45 minute restriction digest the mixture is applied to a sequencing gel. Thus, the work involved in obtaining sequence information from the originally uninformative time points is minimal.

The foregoing specification, including the specific embodiments and examples, is illustrative of the present invention and is not intended to limit the invention in any way. It will be apparent to those skilled in the art that numerous variations and modifications to the above-described embodiments of the invention will be possible without departing from the spirit and scope of the invention. It is intended that the following claims be interpreted to embrace all such variations and modifications.

What is claimed is:

1. An improved method of determining the nucleotide base sequence of DNA comprising the steps of:
   (a) preparing a DNA substrate comprising a set of molecules, each molecule having a template strand and a primer strand, wherein the 3' ends of said primer strands terminate at about the same nucleotide position on said template strands of said molecules within said set;
   (b) inducing DNA synthesis to obtain labeled reaction products comprising newly synthesized DNA complementary to said template strands using the 3' ends of said primer strands to prime DNA synthesis, labeled nucleoside triphosphates, and at least one modified nucleoside triphosphate, wherein said modified nucleoside triphosphate is selected to substantially protect newly synthesized DNA from cleavage;
   (c) cleaving said labeled reaction products at a selected site or sites to obtain labeled DNA fragments wherein said newly synthesized DNA is substantially protected from cleavage at said site or sites; and
   (d) separating said labeled DNA fragments obtained in step (c) and thereafter identifying their nucleotide base sequence by suitable means.

2. The method according to claim 1 wherein said DNA to be sequenced is a double stranded DNA molecule.

3. The method according to claim 2 wherein step (a) comprises contacting said double stranded DNA molecule with an exonuclease capable of deleting DNA from the 3' end of one or both strands of said double stranded DNA molecule.

4. The method according to claim 3 wherein said double stranded DNA molecule is contacted with said exonuclease for times and under conditions sufficient to produce differing sets of molecules having strands of varying lengths.

5. The method according to claims 3 or 4 wherein said exonuclease is *E. coli* exonuclease III.

6. The method according to claim 1 wherein said DNA to be sequenced is a single stranded DNA molecule.

7. The method according to claim 6 wherein step (a) comprises contacting said single stranded DNA molecule with a DNA polymerase suitable for synthesis of DNA complementary to said single stranded DNA.

8. The method according to claim 7 wherein said single stranded DNA molecule is contacted with said DNA polymerase for times and under conditions sufficient to produce differing sets of molecules having strands of varying lengths.

9. The method according to claim 1 wherein said modified nucleoside triphosphate is selected to substantially protect said newly synthesized DNA from cleavage by a restriction endonuclease.

10. The method according to claim 1 wherein said modified nucleoside triphosphate is selected to substantially protect said newly synthesized DNA from cleavage by a chemical reagent.

11. The method according to claim 9 wherein said modified nucleoside triphosphate is a methyl-deoxynucleoside triphosphate.

12. The method according to claim 9 wherein said modified nucleoside triphosphate is an alpha-thio-deoxynucieoside triphosphate.

13. The method according to claim 11 wherein said methyldeoxynucleoside triphosphate is 5-methyl dCTP.

14. The method according to claim 11 wherein said methyldeoxynucleoside triphosphate is 7-methyl dATP.

15. The method according to claim 1 wherein said labeled nucleoside triphosphates are radioactively labeled.

16. The method according to claim 1 wherein said labeled nucleoside triphosphates are fluorescently labeled.

17. The method according to claim 1 wherein said labeled nucleoside triphosphates are biotinylated.

18. The method according to claim 1 wherein step (b) further comprises inducing DNA synthesis in the presence of a suitable chain terminator to obtain labeled chain terminated reaction products.

19. The method according to claim 18 wherein said chain terminator is a dideoxynucleoside triphosphate.

20. The method according to claim 1 wherein step (b) comprises inducing DNA synthesis using limiting amounts of nucleoside triphosphates sufficient to permit DNA synthesis to stall, and thereafter permitting DNA synthesis to continue in the presence of said modified nucleoside triphosphate but without said labeled nucleoside triphosphates.

21. The method according to claim 1 wherein step (b) further comprises inducing DNA synthesis using a suitable DNA synthesis inducing agent selected from the group consisting of Klenow fragment of *E. coli* DNA polymerase I, Taq DNA polymerase, T7 DNA polymerase, and reverse transcriptase.

22. The method according to claims 3 or 4 wherein step (a) further comprises inserting said double stranded DNA into a vector having first and second restriction sites on at least one side of said DNA insert and cleaving said vector with a first restriction endonuclease selected to cleave at said first site and a second restriction endonuclease selected to cleave at said second site to produce a linear double stranded DNA molecule, said first and second restriction sites being present on one side of said DNA insert and said first site being adjacent to said second site and distal to said DNA insert, wherein said second restriction endonuclease is selected to leave a 5' overhang or blunt end to permit exonuclease digestion.

23. The method according to claims 3 or 4 wherein step (a) further comprises inserting said double stranded DNA into a vector comprising a first restriction site and cleaving said vector with a first restriction endonuclease selected to cleave at said first restriction site to produce a linear double stranded DNA molecule, wherein said first restriction endonuclease is selected to leave a 5' overhang or blunt end to permit exonuclease digestion.

24. The method according to claim 23 wherein said vector is substantially incapable of being cleaved at the selected site or sites at which said labeled reaction products obtained during step (b) are cleaved to produce labeled DNA fragments.

25. The method according to claims 3 or 4 wherein step (a) further comprises inserting said double stranded DNA into a vector comprising at least one selected recognition sequence derived from a suitable bacteriophage and nicking one strand of the double stranded vector DNA with an enzyme capable of recognizing and nicking said selected recognition sequence wherein the 3' end of said nicked strand permits exonuclease digestion.

26. The method according to claim 25 wherein said selected recognition sequence is derived from an fl bacteriophage and said enzyme capable of recognizing and nicking said selected recognition sequence is the gene II protein derived from said bacteriophage.

27. The method according to claim 25 wherein said selected recognition sequence is derived from a phi X bacteriophage and said enzyme capable of recognizing and nicking said selected recognition sequence is the gene A protein derived from said bacteriophage.

28. The method according to claims 3 or 4 wherein step (a) further comprises preparing a double stranded polymerase chain reaction (PCR) amplified DNA product using a first PCR amplification primer and a second PCR amplification primer.

29. The method according to claim 28 wherein either or both of said first and second PCR amplification primers are selected to substantially block exonuclease digestion from one end of said double stranded PCR amplified DNA product.

30. The method according to claim 29 wherein either or both of said first and second PCR amplification primers are selected to hybridize to the DNA to be sequenced.

31. The method according to claim 29 wherein either or both of said first and second PCR amplification primers are selected to hybridize to a vector sequence proximal to a site in which the DNA to be sequenced is inserted.

32. A kit useful for the determination of the nucleotide sequence of DNA comprising an exonuclease capable of deleting DNA from the 3' end of one or both strands of a double stranded DNA molecule and at least one modified nucleoside triphosphate selected to substantially protect newly synthesized DNA into which it is incorporated from cleavage.

33. The kit according to claim 32 wherein said modified nucleoside triphosphate is a methyl deoxynucleoside triphosphate.

34. The kit according to claim 31 wherein said methyl deoxynucleoside triphosphate is a 5-methyl dCTP and said exonuclease is *E. coli* exonuclease III.

35. An improved method of determining the nucleotide base sequence of a nucleic acid comprising the steps of:
   a) preparing a nucleic acid substrate comprising a set of molecules, each molecule having a template strand and a primer strand, wherein the 3' ends of said primer strands terminate at about the same nucleotide position on said template strands of said molecules within said set;
   (b) inducing nucleic acid synthesis to obtain labeled reaction products comprising newly synthesized nucleic acid complementary to said template strands using the 3' ends of said primer strands to prime nucleic acid synthesis, labeled nucleoside triphosphates, and at least one modified nucleoside triphosphate, wherein said modified nucleoside triphosphate is selected to substantially protect newly synthesized nucleic acid from cleavage;
   (c) cleaving said labeled reaction products at a selected site or sites to obtain labeled nucleic acid fragments, said newly synthesized nucleic acid being substantially protected from cleavage at said site or sites; and
   (d) separating said labeled nucleic acid fragments obtained in step (c) and thereafter identifying their nucleotide base sequence by suitable means.

36. The method according to claim 35 wherein said DNA substrate comprises a set of molecules, each molecule having a template strand and a primer strand, wherein said template strands and said primer strands are of unequal lengths and the 3' ends of said primer strands terminate at about the same nucleotide position on said template strands of said molecules within said set.

* * * * *